US012623199B2

(12) United States Patent
Tu et al.

(10) Patent No.: US 12,623,199 B2
(45) Date of Patent: May 12, 2026

(54) PLASMA CONVERSION REACTOR OF C02 WITH C1 TO C4 HYDROCARBON TO C1 TO C5 OXYGENATE AND METHOD THEREOF

(71) Applicant: THE UNIVERSITY OF LIVERPOOL, Liverpool (GB)

(72) Inventors: Xin Tu, Liverpool (GB); Yaolin Wang, Liverpool (GB)

(73) Assignee: THE UNIVERSITY OF LIVERPOOL, Liverpool (GB)

( * ) Notice: Subject to any disclaimer, the term of this patent is extended or adjusted under 35 U.S.C. 154(b) by 629 days.

(21) Appl. No.: 18/001,771

(22) PCT Filed: Jun. 15, 2021

(86) PCT No.: PCT/GB2021/051481
§ 371 (c)(1),
(2) Date: Dec. 14, 2022

(87) PCT Pub. No.: WO2021/255423
PCT Pub. Date: Dec. 23, 2021

(65) Prior Publication Data
US 2023/0234017 A1    Jul. 27, 2023

(30) Foreign Application Priority Data
Jun. 15, 2020    (GB) .................................. 2009095.7

(51) Int. Cl.
*B01J 19/08*        (2006.01)
*C07C 29/48*        (2006.01)
*C07C 51/215*       (2006.01)

(52) U.S. Cl.
CPC ............. *B01J 19/088* (2013.01); *C07C 29/48* (2013.01); *C07C 51/215* (2013.01); *B01J 2219/0896* (2013.01)

(58) Field of Classification Search
CPC ............................... B01J 19/088; C07C 29/48
See application file for complete search history.

(56) References Cited

FOREIGN PATENT DOCUMENTS

CN      109529851 A    3/2019
CN      110394127 A    11/2019
CN      110560032 A    12/2019

OTHER PUBLICATIONS

PCT International Search Report and Written Opinion for International Application No. PCT/GB2021/051481, dated Oct. 1, 2021, 11 pages.
Great Britain Search Report for Application No. GB2009095.7, dated Dec. 7, 2020, 4 pages.
Wang et al., "Atmospheric Pressure and Room Temperature Synthesis of Methanol through Plasma-Catalytic Hydrogenation of CO2," ACS Catalysis, vol. 8, 2018, pp. 90-100.
Wang et al., "One-Step Reforming of CO2 and CH4 into High-Value Liquid Chemicals and Fuels at Room Temperature by Plasma-Driven Catalysis," Angew. Chem. Int. Ed., vol. 56, 2017, pp. 13679-13683.
Li et al., "Direct conversion of CO2 and CH4 into liquid chemicals by plasma-catalysis," Applied Catalysis B: Environmental, Elsevier, vol. 261, 2019, 8 pages.
Wang et al., "Supporting Information One-Step Reforming of CO2 and CH4 into High-Value Liquid Chemicals and Fuels at Room Temperature by Plasma-Driven Catalysis," Angew. Chem. Int. Ed., 2017, pp. 1-100.

*Primary Examiner* — Shawquia Jackson
(74) *Attorney, Agent, or Firm* — Hoffman Warnick LLC

(57) ABSTRACT

An apparatus for forming a C1 to C5 oxygenate from carbon dioxide and a C1 to C4 hydrocarbon is described. The apparatus comprises: a dielectric barrier discharge, DBD, device arranged to generate a plasma; and a passageway having an inlet for the carbon dioxide and the C1 to C4 hydrocarbon and an outlet for the oxygenates. In one example the passageway includes therein a catalyst. The passageway extends, at least in part, through the DBD device wherein, in use, the carbon dioxide in reacted with the C1 to C4 hydrocarbon in the generated plasma, thereby forming the oxygenates from at least some of the carbon dioxide and the C1 to C4 hydrocarbon. The DBD device comprises a conducting liquid as a ground electrode. A method and a use are also described.

14 Claims, 14 Drawing Sheets

PLASMA CONVERSION REACTOR OF C02 WITH C1 TO C4 HYDROCARBON TO C1 TO C5 OXYGENATE AND METHOD THEREOF

FIELD

The present invention relates to apparatus and methods, for example apparatus and methods for use in carbon dioxide hydrogenation processes. Particularly, the present invention relates to an apparatus and method for use in carbon dioxide reforming of a C1 to C4 hydrocarbon to a C1 to C5 oxygenate using a non-thermal plasma generated by dielectric barrier discharge (DBD).

BACKGROUND TO THE INVENTION

The conversion and utilization of $CO_2$, an increasingly attractive C1 building block, not only contributes to alleviating global climate changes induced by the increasing $CO_2$ emissions but also opens up new sustainable routes for synthesizing useful feedstock chemicals and fuels. Direct transformation of hydrocarbons (especially methane) into value-added chemicals is a "holy grail" in chemistry. It is particularly challenging to perform selective conversion of hydrocarbons (especially methane) to oxygenates under mild conditions.

As $CO_2$ and hydrocarbons are thermodynamically stable molecules, considerable efforts have been devoted to activating the C=O, C—C and C—H bonds and converting to more valuable products efficiently over the past decades.

The catalytic reforming of hydrocarbons (e.g. a C1 to C4 hydrocarbon) with $CO_2$, however, remains challenging, primarily because of the chemical inertness of these molecules. Therefore, high temperature and/or high pressure is usually required to overcome the activation barrier during conventional catalytic conversions. Direct transformation of a C1 to C4 hydrocarbon with $CO_2$ to oxygenates is very challenging and almost impossible under milder conditions, thus this process remains a well-known 'holy grail' in chemistry. Thermal catalytic $CO_2$ reforming with a C1 to C4 hydrocarbon to oxygenates using an indirect route often proceeds through two steps: i) $CO_2$ reforming of hydrocarbons to produce syngas at high temperatures due to thermodynamic barrier of this reaction; 2) conversion of syngas to oxygenates at high pressure and relatively high temperature. The first step for syngas production is highly endothermic and requires high temperatures and energy input. It is almost impossible to directly convert hydrocarbons with $CO_2$ to oxygenates in a single step bypassing the generation of syngas.

Non-thermal plasmas have been employed as a highly promising approach for converting a wide range of stable C-containing molecules to syngas, alcohols and oxygenates in a single step under low temperature and ambient pressure. The energetic electrons can activate molecules via excitation, dissociation and ionization. The reactive species (i.e. radicals, ions, excited species) generated in the plasma contribute to both the gas phase reactions and surface reactions, initiating new reaction pathways at low temperatures and ambient pressure. The use of a catalyst in the plasma process has great potential to enhance the selectivity towards target products. Plasma catalysis provides a promising and alternative for the single step selective production of a C1 to C5 oxygenate via $CO_2$ reforming of a C1 to C4 hydrocarbon at near room temperature and ambient pressure.

SUMMARY OF THE INVENTION

It is one aim of the present invention, amongst others, to provide an apparatus and method for converting carbon dioxide and a C1 to C4 hydrocarbon into a C1 to C5 oxygenate, which at least partially obviates or mitigates at least some of the disadvantages of the prior art, whether identified herein or elsewhere. For instance, it is an aim of embodiments of the invention to provide an apparatus to provide plasma-activated synthesis of a C1 to C5 oxygenate from carbon dioxide and a C1 to C4 hydrocarbon, with a high conversion of reactants, high selectivity and/or yield of oxygenates and/or high energy efficiency.

For instance, it is an aim of embodiments of the invention to provide a method of synthesising a C1 to C5 oxygenate from carbon dioxide and a C1 to C4 hydrocarbon at low temperature or room temperature and atmospheric pressure using plasma. For instance, it is an aim of embodiments of the invention to provide an apparatus for and/or a method of carbon dioxide reforming or oxidative coupling of hydrocarbons using soft oxidant $CO_2$ that does not require additional heating and can be conducted at ambient pressure. For instance, it is an aim of embodiments of the invention to provide an apparatus for and/or a method of carbon dioxide reforming that may be integrated with renewable energy sources (e.g. wind and solar power), especially the use of intermittent renewable energy during peak load for localised or distributed energy storage.

DETAILED DESCRIPTION OF THE INVENTION

According to the present invention there is provided an apparatus, as set forth in the appended claims. Also provided is a method and a use. Other features of the invention will be apparent from the dependent claims, and the description that follows.

Apparatus

A first aspect provides an apparatus for forming a C1 to C5 oxygenate from carbon dioxide and a C1 to C4 hydrocarbon or a mixture thereof, the apparatus comprising:

a dielectric barrier discharge, DBD, device arranged to generate a plasma; and a passageway including an inlet for the carbon dioxide and the C1 to C4 hydrocarbon and an outlet for the oxygenates, wherein the passageway extends, at least in part, through the DBD device wherein, in use, the carbon dioxide and the C1 to C4 hydrocarbon are reacted in the generated plasma, thereby forming the oxygenates from at least some of the carbon dioxide and the C1 to C4 hydrocarbon and wherein the DBD device comprises a conducting liquid electrode.

The apparatus is suitable for forming one or more 1 to C5 oxygenates from carbon dioxide and one or more C1 to C4 hydrocarbons, for example a mixture of C1 to C4 hydrocarbons sourced from nature gas, shale gas, biogas. The apparatus is suitably for forming liquid oxygenates from carbon dioxide and a C1 to C4 hydrocarbon. For the avoidance of doubt, the carbon dioxide and the C1 to C4 hydrocarbon are provided in gaseous form. Any C1 to C4 hydrocarbon may be used. The C1 to C4 hydrocarbon may be saturated or unsaturated. The C1 to C4 hydrocarbon may be linear or branched. In one example, the C1 to C4 hydrocarbon is selected from methane, ethane or propane.

Other gaseous products may be formed, for example hydrogen, carbon monoxide and/or other short chain gaseous hydrocarbons such as methane if use C2+ hydrocarbons. Other liquid products may be formed, such as ethanol and ethanoic acid. However, these other products can be separated and/or removed. In one example, the apparatus comprises a separation unit for separating oxygenates. In one preferred example, methanol is formed as the major liquid product.

The apparatus comprises the DBD device comprising a conducting liquid, for example water, an aqueous solution such as of metal salts, an ionic liquid as a ground electrode.

Generally, DBDs are self-sustaining electrical discharges between electrodes having an insulating material (i.e. the dielectric barrier) in the discharge path (also known as a discharge zone). The dielectric is responsible for self-pulsing of the plasma, resulting in a non-thermal plasma at ambient pressures. Typically, dielectrics include glass, quartz, ceramics, enamel, mica, polymeric compositions and silicon rubber. Other dielectrics are known. The discharge gap is typically 1 to 10 mm, so as to allow operation at ambient pressures and moderate voltage amplitudes. Alternating current or pulsed high-voltage, typically in a range from about 1 kV to 100 kV at frequencies in a range from about 50 Hz to 1 MHz, are required due to the capacitive properties of the electrode and dielectric assembly. DBD reactors with planar configurations and axial electrode arrangements are often used for chemical reactions.

In one example, the DBD device comprises a set of electrodes, including a first electrode and a second electrode, having a dielectric barrier therebetween. The DBD device comprises a liquid electrode as a ground electrode. This may be referred to herein as the first electrode. The DBD device also comprises a second electrode.

In one example, the set of electrodes is arranged in a coaxial configuration. In one example, the DBD device comprises a coaxial DBD. In this way, an annular discharge zone may be formed.

In one example, the first electrode comprises and/or is a first tube, for example a cylindrical tube, and the second electrode comprises and/or is a wire, a rod or a second tube, for example a cylindrical tube, coaxial therewithin, wherein the dielectric barrier is in contact with the first electrode or the second electrode. In other words, the first electrode may be an outer tube and the second electrode may be an inner wire. For example, the dielectric barrier may be provided on internal surfaces of the first electrode, in which the plasma is formed in the gas at the surface of the dielectric barrier and propagates radially across a volume to the second electrode. Additionally and/or alternatively, the dielectric barrier may be provided on outer surfaces of the second electrode, in which the plasma is formed in the gas at the surface of the dielectric barrier and propagates readily across a volume to the first electrode.

It should be understood that the electrodes are thus electrical conductors. In one example, the second electrode comprises and/or is a metallic electrode, for example a metal or alloy. In one example, the second electrode comprises and/or is a metallic plate, sheet, film or wire electrode. For example, the second electrode may be provided by solid metal plate or sheet, by printing metal films on the dielectric, by etching of circuit boards, by depositing metallic film or paste on the dielectric or by using wire mesh, for example. Other electrodes are known.

Any suitable liquid may be used as the ground electrode. In one example, the liquid is selected from water, ionic liquid, metal salts solutions. In one example, the liquid is water.

In one example, the first electrode comprises and/or is a non-metal cylinder filled with circulating cooling liquid, for example cooling water. The inner surface of this cylinder can be used as dielectric barrier.

In one example, the dielectric barrier comprises and/or is glass, quartz, ceramic, enamel, mica, a polymeric composition and/or silicon rubber. Suitable glasses include silicate glass, such as soda lime glass, borosilicate glass, lead glass, aluminosilicate glass, and silica-free glass.

In one example, the DBD device comprises: a quartz tube (i.e. providing the passageway) having a gas inlet (i.e. the inlet) in an upper portion thereof and the outlet in a lower portion thereof; an inner electrode having, for example, a cylindrical rod shape and provided in the quartz glass tube; an outer electrode, for example water, around at least in part the outer surface of the quartz glass tube; and a catalyst contained in the quartz glass tube between the inner electrode and the outer electrode (i.e. a coaxial configuration).

In one example, the inner electrode comprises and/or is a stainless steel rod or wire and the outer electrode comprises and/or is a cylindrical tubular stainless-steel mesh coaxial therewith.

In one example, the apparatus comprises a gas supply unit for supplying the carbon dioxide ($CO_2$) gas and the C1 to C4 hydrocarbon gas.

In one example, the gas supply unit further supplies nitrogen ($N_2$) or argon (Ar) gas to generate, at least in part, the DBD plasma. However, this may not be preferred. In one preferred example, no further gas is supplied to generate the DBD plasma.

It has surprisingly been found by the inventors that an apparatus comprising a DBD comprising a liquid ground electrode is particularly suitable for plasma $CO_2$ reforming of methane to methanol. In one example, the apparatus of the first aspect, when in use, obtains a high $CO_2$ conversion and methane, methanol selectivity, methanol yield and/or energy efficiency without using any heating equipment.

In one example, the apparatus may be used without a catalyst.

In one example, the apparatus may include a catalyst. Any suitable catalyst may be used. In one example, the passageway includes a catalyst provided therein.

In one example, the catalyst comprises an oxide selected from $TiO_2$, $CeO_2$, $SiO_2$, $Al_2O_3$ or $ZrO_3$. In one example, the catalyst comprises a zeolite or zeotype material, for example ZSM-5 or SAPO (a silico-alumino-phosphate).

In one example, the alumina comprises and/or is $\gamma$-$Al_2O_3$. $\gamma$-$Al_2O_3$ is preferred to $\alpha$-$Al_2O_3$, for example, having a higher Brunauer-Emmett-Teller (BET) surface area. Activated $Al_2O_3$ may also be used.

In one example, the catalyst comprises and/or is a zeolite structure. In one example, the zeolite structure comprises and/or is ZSM-5.

In one example, hierarchical ZSM-5 nanocrystals may be used. Suitably the ZSM-5 may comprise different Si/Al ratios. Such ratios are known to the skilled person and are commonly referred to in brackets, for example ZSM-5 (28).

In one example, the catalyst comprises a transition metal. In one example, the transition metal is selected from the group consisting of zinc, iron, copper, nickel, cobalt, cerium and mixtures thereof. In one example, the catalyst comprises a transition metal oxide. In one example, the catalyst comprises a transition metal oxide selected from zinc oxide, copper oxide, cerium oxide, iron oxide and nickel oxide.

In one example, the catalyst is provided in the form of particles, granules, pellets, tablets plates and/or conglomerates thereof. In one example, the catalyst is provided in the form of particles, for example, granules, having an average particle diameter in a range from 0.05 mm to 1.0 mm, preferably in a range from 0.1 mm to 0.75 mm, more preferably in a range from 0.25 mm to 0.50 mm. These could be controlled by sieves. Other methods of measuring the average particle diameter will be known by the skilled person. Catalysts can be fully packed in the discharge zone or partially packed in the discharge zone. Porous catalytic materials are preferable to reduce the pressure drop in the plasma reactor.

In one example, the transition metal is held on a support. It should be understood that the transition metal is affixed to the support. For example, the transition metal may be impregnated in the support (i.e. prepared by impregnation). Additionally and/or alternatively, the catalyst comprising a transition metal held on a support may be prepared by co-precipitation.

In one example, the support comprises and/or is selected from the group consisting of $SiO_2$, $TiO_2$, $Al_2O_3$, $CeO_2$, $ZrO_2$, ZnO, $Cr_2O_3$, carbon nanotubes, $Ga_2O_3$, $In_2O_3$ and zeolite. In one example, the support comprises and/or is alumina ($A_2O_3$), as described above.

In one example, the catalyst comprises a transition metal in a range from 1 to 20 wt. %, preferably in a range from 1 to 15 wt. %, more preferably in a range from 2 to 12 wt. %, even more preferably in a range from 5 to 10 wt. % transition metal by weight of the catalyst.

In one example, the catalyst comprises a transition metal in a range from 1 to 20 wt. %, preferably in a range from 1 to 15 wt. %, more preferably in a range from 2 to 12 wt. %, even more preferably in a range from 5 to 10 wt. % cobalt by weight of the support, if present.

In one example, the catalyst consists essentially (at least 99 wt. % by weight of the catalyst) or consists (at least 99.9 wt. % by weight of the catalyst) of transition metal (for example, nickel and/or cobalt), any support and unavoidable impurities. Unavoidable impurities include, for example, other metals.

In one example, the catalyst is prepared using incipient wetness impregnation (IW or IWI), which is also known in the art as capillary impregnation or dry impregnation. In one example, a nickel and/or cobalt precursor is dissolved in an aqueous solution and the nickel-containing and/or cobalt-containing solution is added to a support. Capillary action draws the solution into the pores. The catalyst may then be dried and optionally calcined to drive off the volatile components within the solution, thereby depositing nickel and/or cobalt on the support surface. Methods of preparing such catalysts are well known. In one example, calcining is performed at a temperature in a range from 400 to 600° C., for a time in a range from 4 hours to 6 hours and/or at a heating rate in a range from 5° C. per minute to 10° C. per minute.

In one example, the catalyst comprises transition metal particles. In one example, the transition metal particles have a mean particle diameter in a range from 1 nm to 15 nm, preferably in a range from 2 nm to 12 nm, more preferably in a range from 3 nm to 10 nm. Generally, smaller particles are preferred. Methods of measuring the mean particle diameter are known, for example, using transmission electron microscopy (TEM) or high-resolution transmission electron microscopy (HRTEM).

In one example, the transition metal particles are evenly distributed, for example dispersed, on the support. In one example, the transition metal particles are uniformly distributed on the support. In one example, the transition metal particles are regularly distributed on the support.

In one example, the transition metal particles are homogenously distributed on the support. The distribution of the transition metal particles may be determined, for example qualitatively and/or quantitatively, using TEM, HRTEM and/or CO adsorption, for example.

In one example, the catalyst comprises other non-transition metal species, such as hydroxyl groups. These species may form in use (i.e. during the reaction).

In one example, the apparatus comprises a source of external heat to provide additional heat to the reaction when in use. However, this is not preferred. In one preferred example, the apparatus does not comprise an or any external heating source(s).

The apparatus may comprise additional safety features. For example, the apparatus may comprise an additional cooling source to reduce temperature when the apparatus is in use. However, this is not preferred. In one particularly preferred example, the liquid from the liquid electrode may be used to cool the reaction. This provides significant advantages in use.

For example, conventional apparatuses often operate at high temperatures and are therefore energy-intensive. Additionally and/or alternatively, conventional apparatus typically require cooling, since direction is exothermic, to attenuate heating. In contrast, the apparatus according to the first aspect may not require additional cooling since the reaction temperature is relatively low and/or the use of a liquid electrode means that liquid can be used to cool the reaction.

Method

A second aspect provides a method of forming a C1 to C5 oxygenate from carbon dioxide and a C1 to C4 hydrocarbon, the method comprising:

generating a plasma using a dielectric barrier discharge device; and reacting the carbon dioxide and the C1 to C4 hydrocarbon in the generated plasma, thereby forming the C1 to C5 oxygenate from at least some of the carbon dioxide and the C1 to C4 hydrocarbon; wherein the DBD device comprises a liquid electrode.

The carbon dioxide, the C1 to C4 hydrocarbon, the plasma, the DBD and the liquid electrode may be as described with respect to the first aspect. The method may include any of the steps and/or features described with respect to the first aspect, mutatis mutandis.

As described with respect to the first aspect, in one example, the DBD comprises a catalyst.

In one example, the reaction temperature (i.e. the temperature at which the carbon dioxide is exposed to the catalyst in the presence of the C1 to C4 hydrocarbon in the generated plasma) is in a range from 15 to 50° C. and more preferably in a range from 18 to 40° C. The reaction temperature may suitably be described as ambient temperature.

In one example, the method comprises externally heating the carbon dioxide, the C1 to C4 hydrocarbon and the catalyst, if present, for example using an external source of heat. In one preferred example, the method comprises no external heating. In this way, the reaction temperature is provided, for example at least partly and/or fully, by the generated plasma.

The method according to the second aspect offers a significant advantage over conventional methods as the reaction may be performed at relatively low temperatures, without an external source of heat. This reduces the energy consumption of the process. Additionally and/or alternatively, it is not necessary to remove heat from the process or provide processes to prevent overheating of the process. This may be because the liquid used in the liquid electrode can be used to cool the reaction to an ambient temperature.

Additionally and/or alternatively, since the reaction may be performed at relatively low temperatures, the method may be initiated (i.e. switched on) and/or paused or terminated (i.e. switched off) on demand, for example immediately or instantly, since preheating is not required, for example.

Since the generated plasma reaches a stable state in a relatively short time, the method may be stopped and subsequently restarted without any additional waiting time, improving an efficiency of the process. In this way, the process provides great flexibility to be integrated with renewable energy sources such as wind and solar power, especially the use of intermittent renewable energy during peak load for localised or distributed energy storage.

In one example, the method comprises activating the catalyst using, at least in part, the generated plasma, for example by supplying an electrical power in a range of 0.72 to 50 kJ/L, preferably in a range of from 10 to 40 kJ/L, relative to the gas flow rate (L) This may also be defined as the specific energy input (SEI).

The conversion $X_{CO_2}$ of carbon dioxide may be defined by Equation (1):

$$X_{CO_2}(\%) = \frac{CO_2 \ \text{converted} \ (\text{mol/s})}{CO_2 \ \text{input} \ (\text{mol/s})} \times 100 \qquad (1)$$

In one example, the method has a conversion $X_{CO_2}$, as defined by equation (1), of carbon dioxide of 10%, preferably at least 20%, more preferably at least 30%.

The conversion of methane $X_{CH_4}$ may be defined by Equation (2):

$$X_{CH_4}(\%) = \frac{CH_4 \ \text{converted} \ (\text{mol/s})}{CH_4 \ \text{input} \ (\text{mol/s})} \times 100 \qquad (2)$$

Suitably the method has a conversion $X_{CH_4}$, as defined by equation (2), of methane of at least 10%, preferably at least 20%, more preferably at least 30%.

The selectivity of methanol $S_{CH_3OH}$ may be defined by Equation (3):

$$S_{CH_3OH}(\%) = \text{Carbon of } CH_3OH \text{ in the liquid products} \times S_{total \ liquid \ products} \qquad (3)$$

In one example, the method has a selectivity $S_{CH_3OH}$ of methanol of at least 20%, preferably at least 30%, most preferably at least 40%, for example at least 50%. In one especially preferred example, the method has a selectivity $S_{CH_3OH}$ of methanol of at least 60%.

In one example, reacting the carbon dioxide and the C1 to C4 hydrocarbon in the generated plasma comprises reacting the carbon and the C1 to C4 hydrocarbon in the generated plasma at approximately ambient pressure. It should be understood that approximately ambient pressure is the substantially natural pressure of the environment, for example about 101 kPa. In one example, the method comprises reacting the carbon dioxide with methane in the generated plasma, thereby forming the methanol from at least some of the carbon dioxide and methane.

In one example, the method comprises reacting the carbon dioxide and the C1 to C4 hydrocarbon in the presence of other gases, for example inert gases such as argon and/or nitrogen and/or reactive gases such as oxygen, amongst others. However, in one preferred example only carbon dioxide and the C1 to C4 hydrocarbon and unavoidable impurities are present, notwithstanding reaction products including methanol.

In one example, reacting the carbon dioxide and the C1 to C4 hydrocarbon in the generated plasma comprises reacting a stoichiometric ratio of the carbon dioxide and the C1 to C4 hydrocarbon (i.e. 1:1). In one example, the ratio of the carbon dioxide to the C1 to C4 hydrocarbon is in a range from 1:3 to 3:1.

In one example, the carbon dioxide and the C1 to C4 hydrocarbon are provided with a total flow rate of 30-70 ml/min. The corresponding residence time is in a range of 2-5.5 s, preferably in a range of 2.5-4 s, most preferably in a range of 3-4 s.

In one example, the method comprises controlling, for example optimising, at least one of a discharge gap distance, a metal of inner electrode, a type of liquid electrode, a discharge length, dielectric materials (e.g. width).

Use

A third aspect provides use of a dielectric barrier discharge device comprising a liquid ground electrode in the plasma-activated reaction of carbon dioxide and a C1 to C4 hydrocarbon to produce a C1 to C5 oxygenate.

The DBD device, the C1 to C5 oxygenate, the carbon dioxide, and/or the C1 to C4 hydrocarbon and/or the plasma, may be as described with respect to the first aspect and/or the second aspect. The use may include any of the steps and/or features described with respect to the first aspect and/or the second aspect, mutatis mutandis.

Catalyst

A fourth aspect provides a catalyst according to the first aspect.

Definitions

Throughout this specification, the term "comprising" or "comprises" means including the component(s) specified but not to the exclusion of the presence of other components. The term "consisting essentially of" or "consists essentially of" means including the components specified but excluding other components except for materials present as impurities, unavoidable materials present as a result of processes used to provide the components, and components added for a purpose other than achieving the technical effect of the invention, such as colourants, and the like.

The term "consisting of" or "consists of" means including the components specified but excluding other components.

Whenever appropriate, depending upon the context, the use of the term "comprises" or "comprising" may also be taken to include the meaning "consists essentially of" or "consisting essentially of", and also may also be taken to include the meaning "consists of" or "consisting of".

The optional features set out herein may be used either individually or in combination with each other where appropriate and particularly in the combinations as set out in the accompanying claims. The optional features for each aspect or exemplary embodiment of the invention, as set out herein are also applicable to all other aspects or exemplary embodiments of the invention, where appropriate. In other words, the skilled person reading this specification should consider the optional features for each aspect or exemplary embodiment of the invention as interchangeable and combinable between different aspects and exemplary embodiments.

BRIEF DESCRIPTION OF THE DRAWINGS

For a better understanding of the invention, and to show how exemplary embodiments of the same may be brought into effect, reference will be made, by way of example only, to the accompanying diagrammatic Figures, in which.

EXAMPLES

Figure 1A:
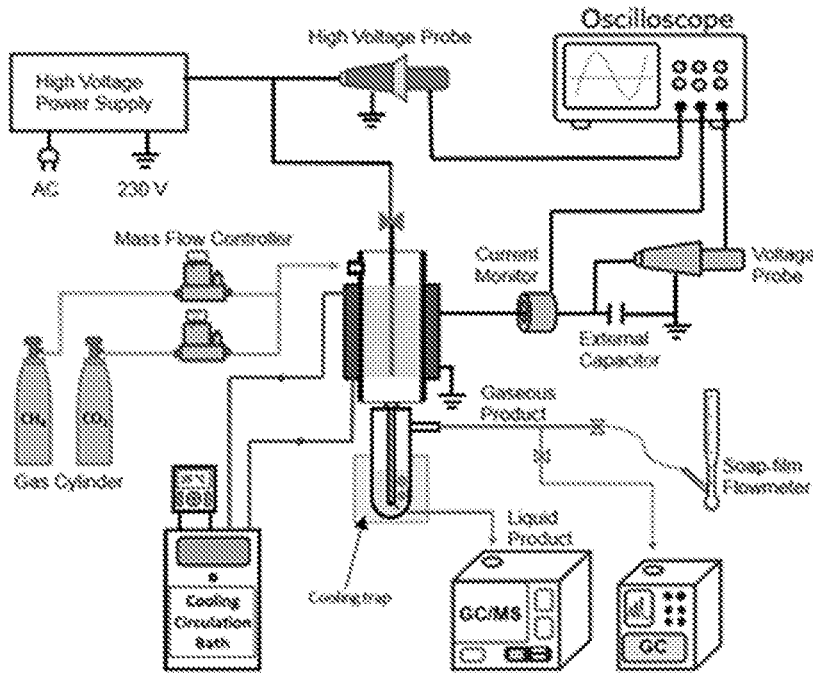
FIGS. 1A and 1B show a schematic diagram of experimental setup.
Figure 1B:
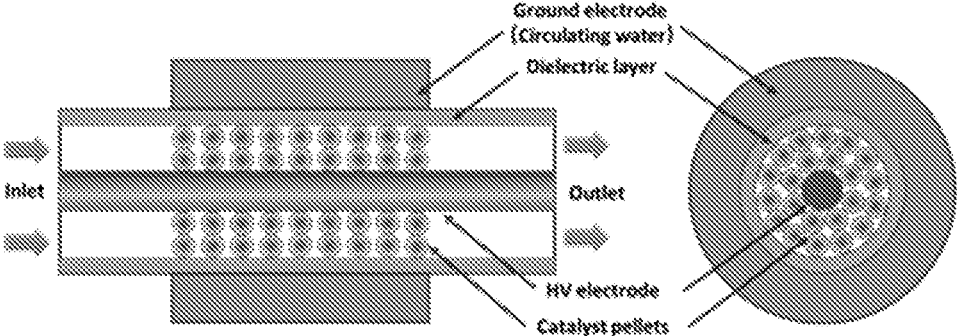

The experiments were conducted in a coaxial DBD reactor with a special and novel electrode design, as shown in FIGS. 1A and 1B. Compared to traditional DBD reactors using metal as a ground electrode, this reactor used circulating water as both a ground electrode and cooling of the reactor. A cooling circulation bath (Grant LT Ecocool 150) was used to control the temperature of the discharge at 20° C. The length of the discharge region was 50 or 30 mm and the discharge gap was 3 or 2 mm. The DBD reactor was connected to an AC high voltage power supply with a peak voltage of up to 30 kV. The DBD discharge power maintained at 20 W and the frequency was fixed at 9.2 kHz. $CO_2$ and $CH_4$ were used as reactants at a total flow rate of 40 or 30 mL/min and a 1:1 molar ratio was used.

The applied voltage of the DBD was measured by a high-voltage probe (TESTEC, HVP-15HF), while the current was recorded by a current monitor (Bergoz, CT-E0.5). The voltage on the external capacitor was used to measure the charge formed in the DBD. All the electrical signals were sampled by a four-channel digital oscilloscope (Tektronix, MDO 3024). A custom system was used to monitor and control the discharge power of the DBD in real-time. The gas temperature in the discharge area near the catalyst bed was measured using a fiber optical thermometer (Omega, FOB102).

The gaseous products were analyzed using a gas chromatograph (Shimadzu GC-2014) equipped with a thermal conductivity detector (TCD) and a flame ionized detector (FID). A water/ice mixture bath was placed at the exit of the DBD reactor to condense liquid products. The oxygenates were qualitatively analyzed using a gas chromatography-mass spectrometer (GC-MS, Agilent GC 7820A and Agilent MSD 5973) and quantitatively analyzed using a gas chromatograph (Agilent 7820) equipped with a FID with a DB-WAX column. The change of the gas volume before and after the reaction was measured using a soap-film flow meter. Sampling and measurements started after running the reaction for 1 h and lasted for 3 h. Each measurement was repeated three times, and the measurement error was less than 4%.

Example 1

The conversion of $CH_4$ and $CO_2$ increases with the increase of SEI (in a range of 15-60 kJ/L).

Figure 2A:
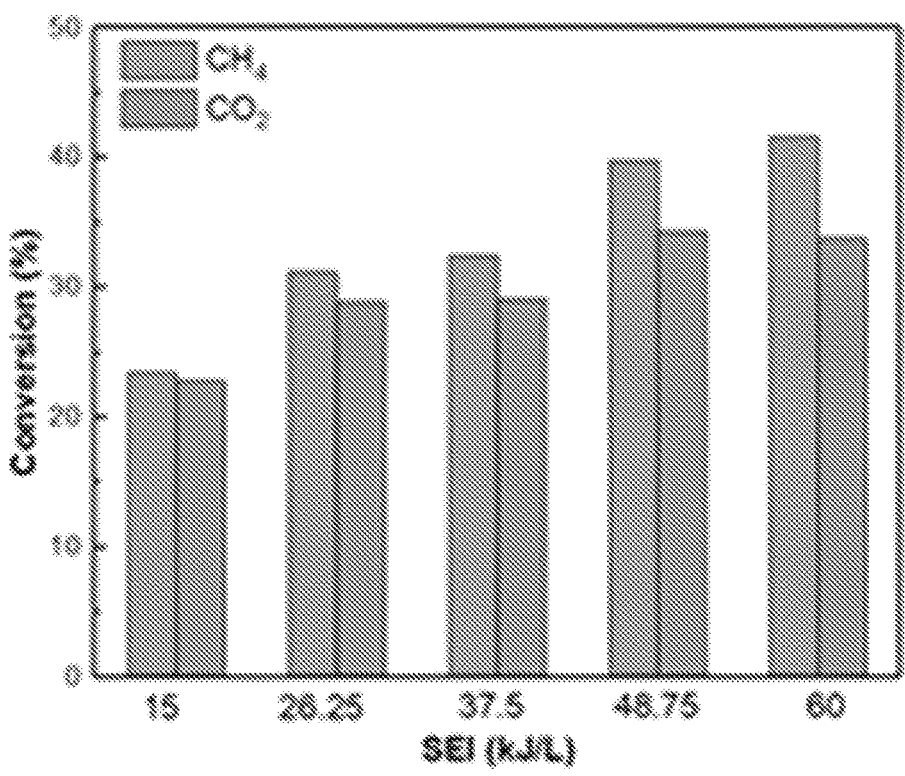
FIGS. 2A to 2D show the effect of specific energy input (SEI) on the synthesis of methanol.
Figure 2B:
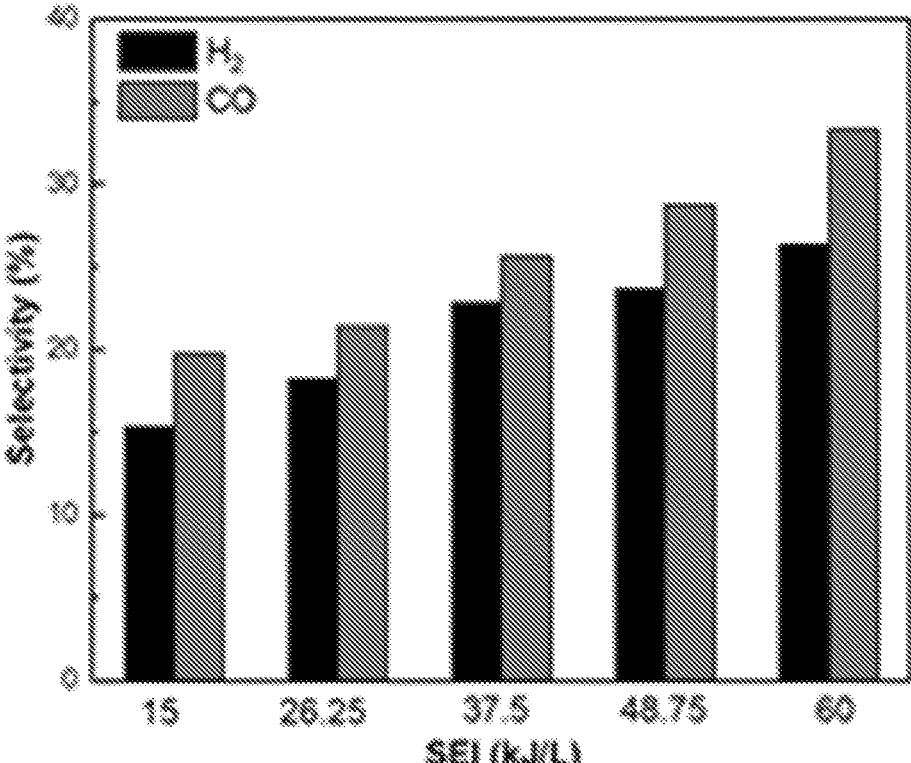
Figure 2C:
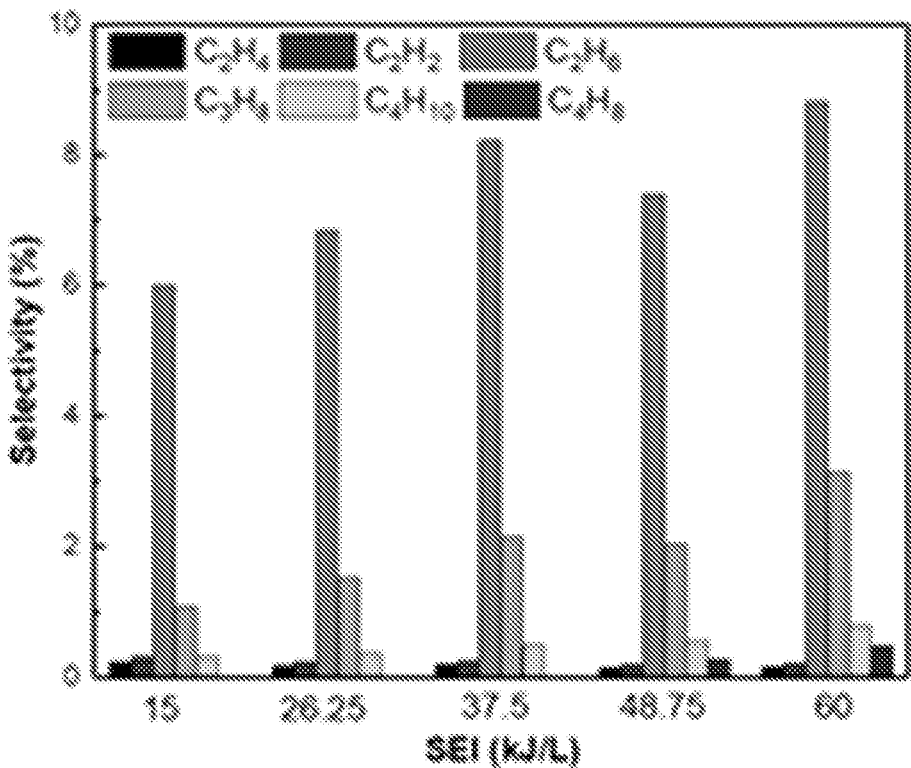
Figure 2D:
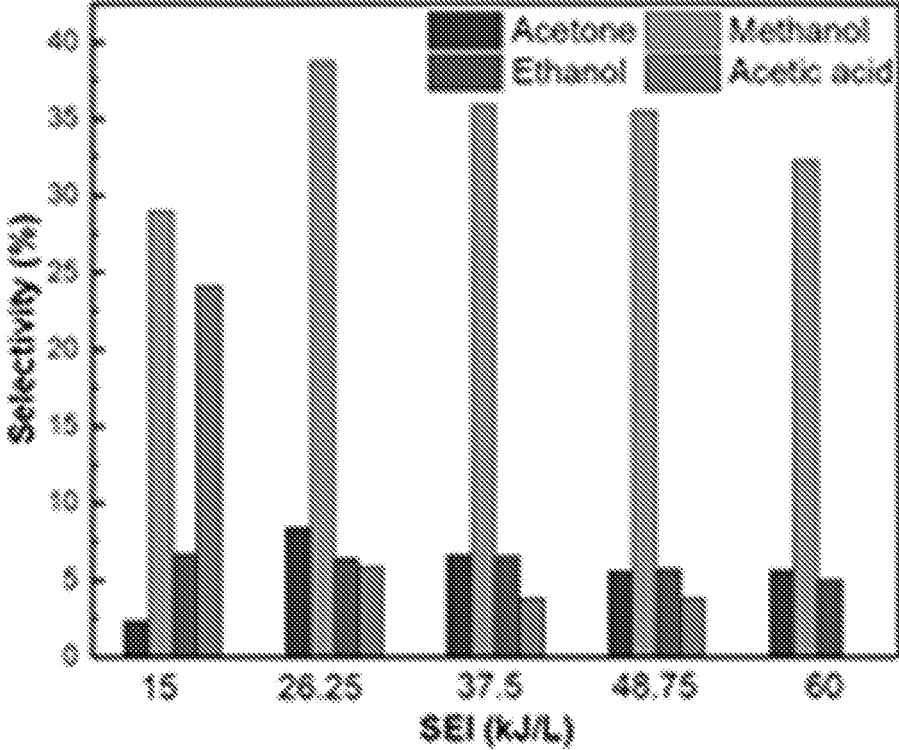

FIG. 2C shows that the distribution of oxygenates can be tuned tailored with the increase of the input powers. Higher power (SEI) leads to generate more gas products and less oxygenates. Methanol, ethanol, acetic acid and acetone are found as major liquid products. Compared to our previous work, the dominant liquid product has been changed from acetic acid to methanol in this study. The highest methanol selectivity reaches 38% at the optimal SEI of 26.3 kJ/L, while the highest selectivity of acetic acid is 24% at a low SEI of 15 kJ/L.

The conversion of $CO_2$ and $CH_4$ is affected by the change of the residence time of the reactants.

Figure 3A:
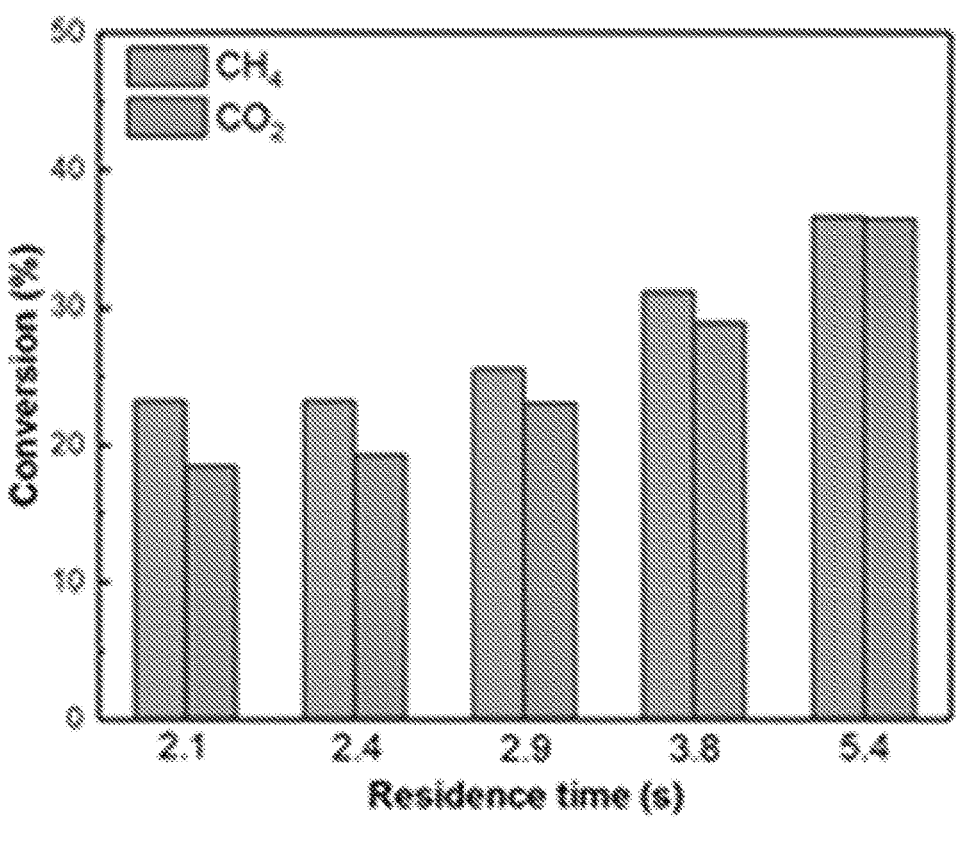
FIGS. 3A to 3D show the effect of different residence times on the reaction.
Figure 3B:
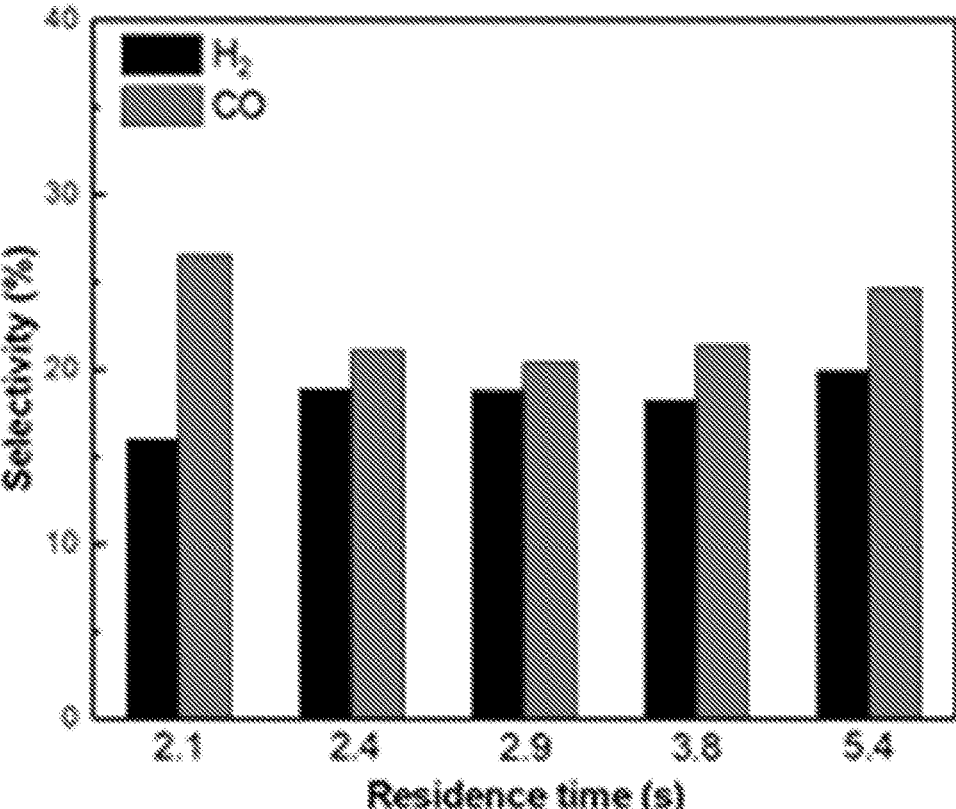
Figure 3C:
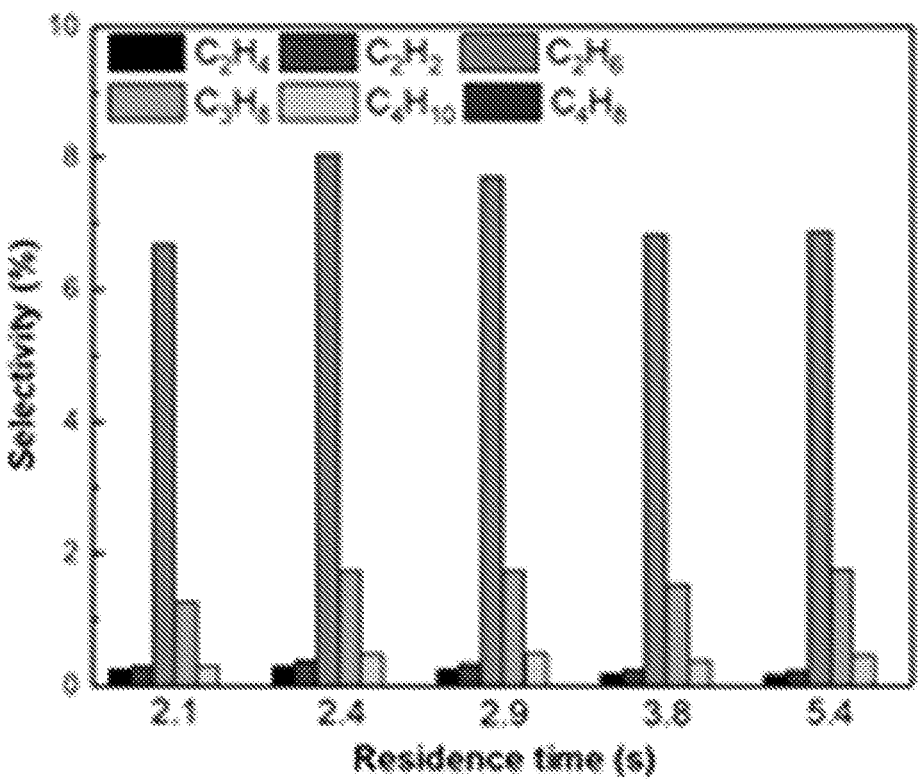
Figure 3D:
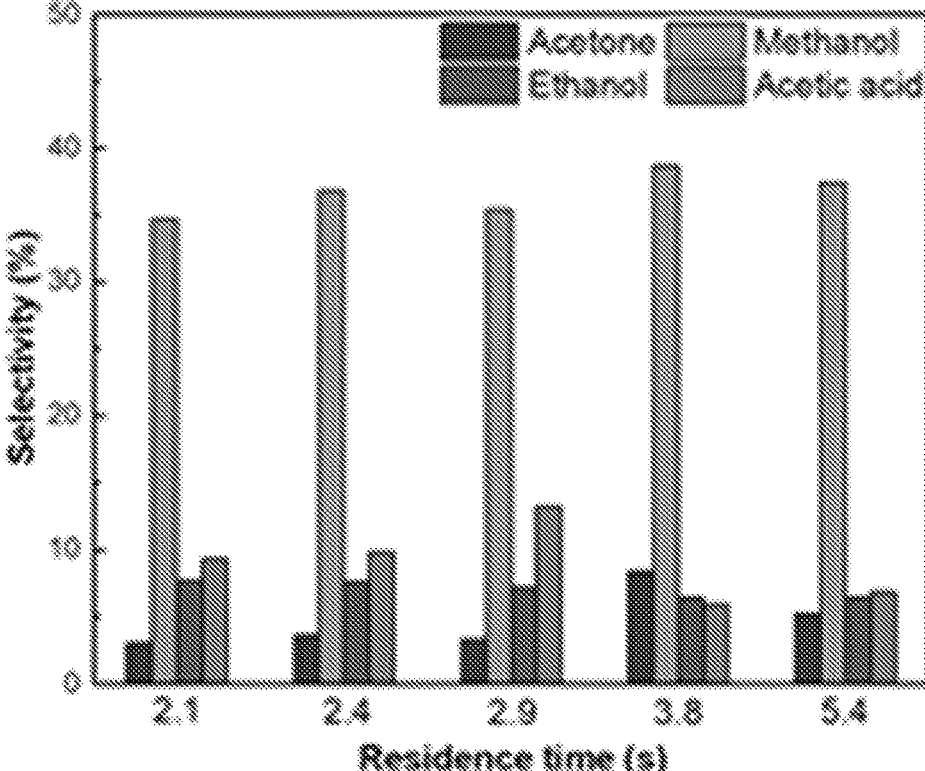
Figure 4A:
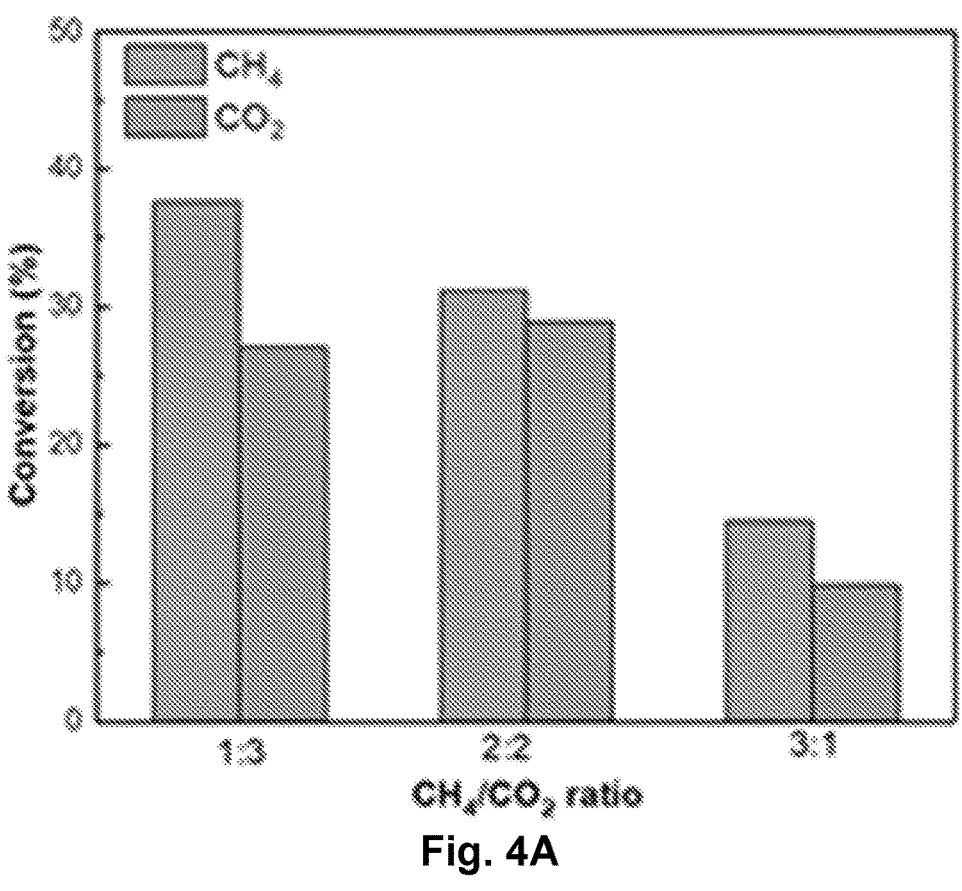
FIGS. 4A to 4D shows the effect of different $CH_4/CO_2$ ratios on the reaction.
Figure 4B:
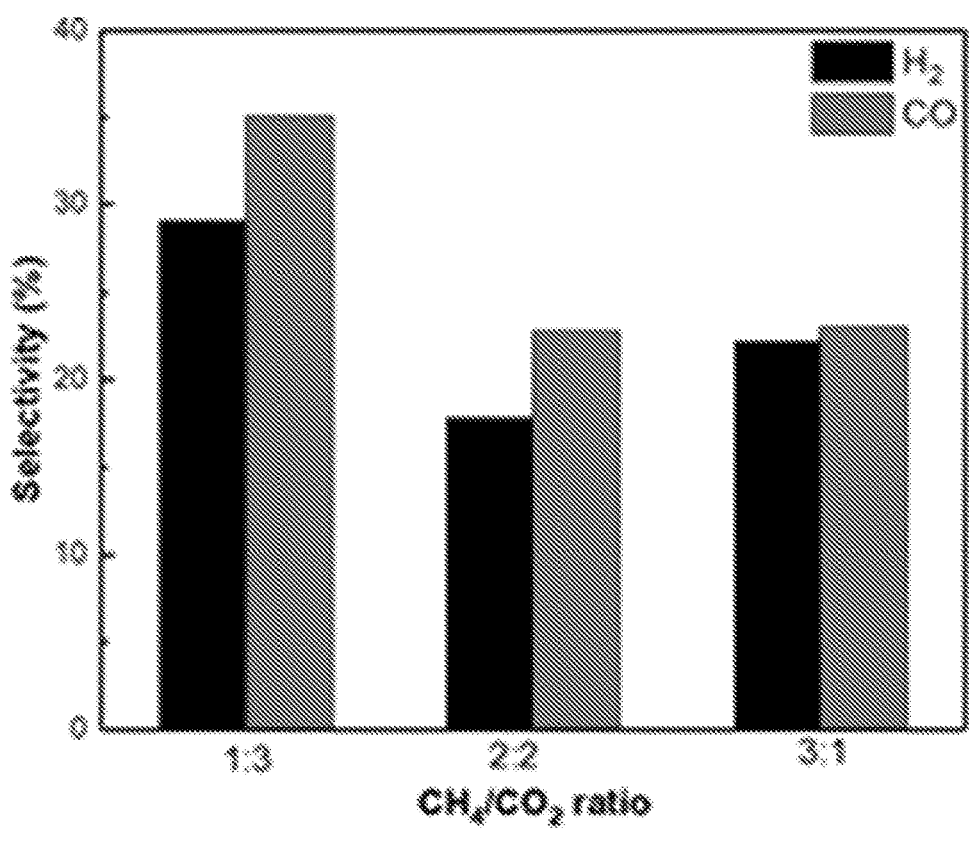
Figure 4C:
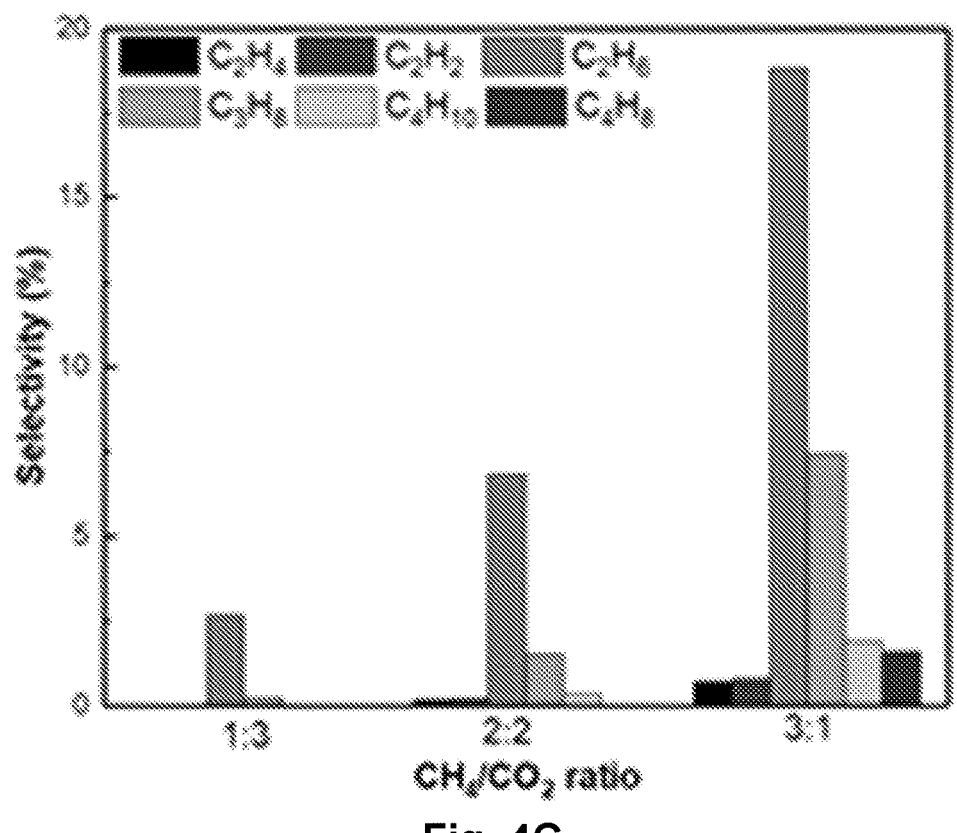
Figure 4D:
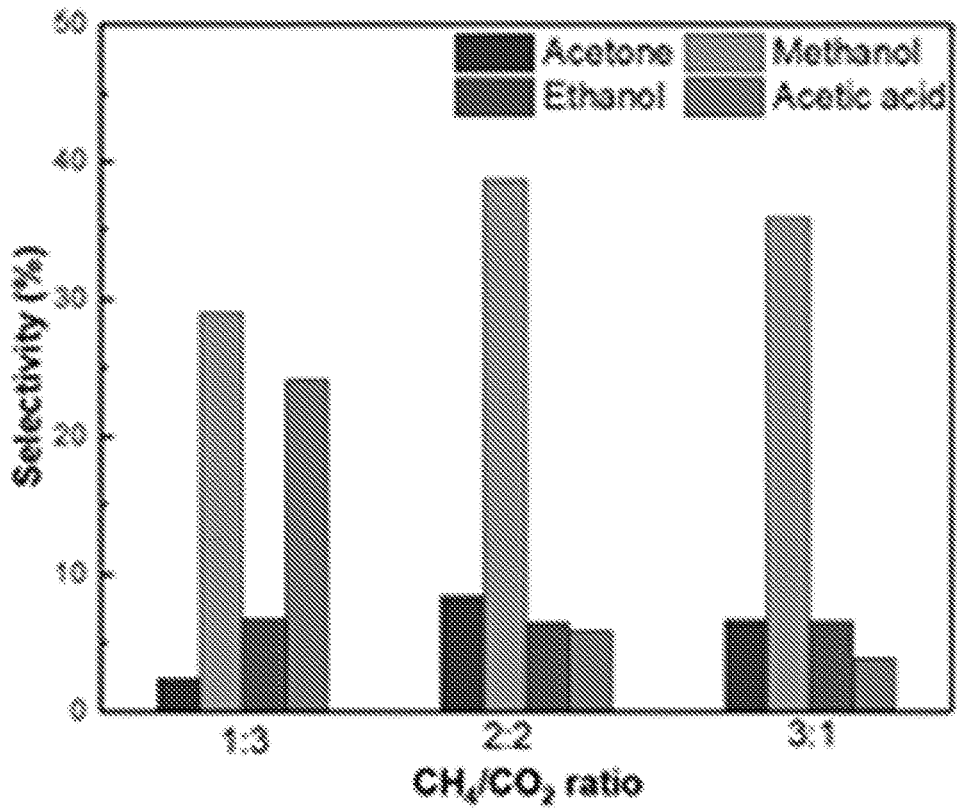
Figure 5A:
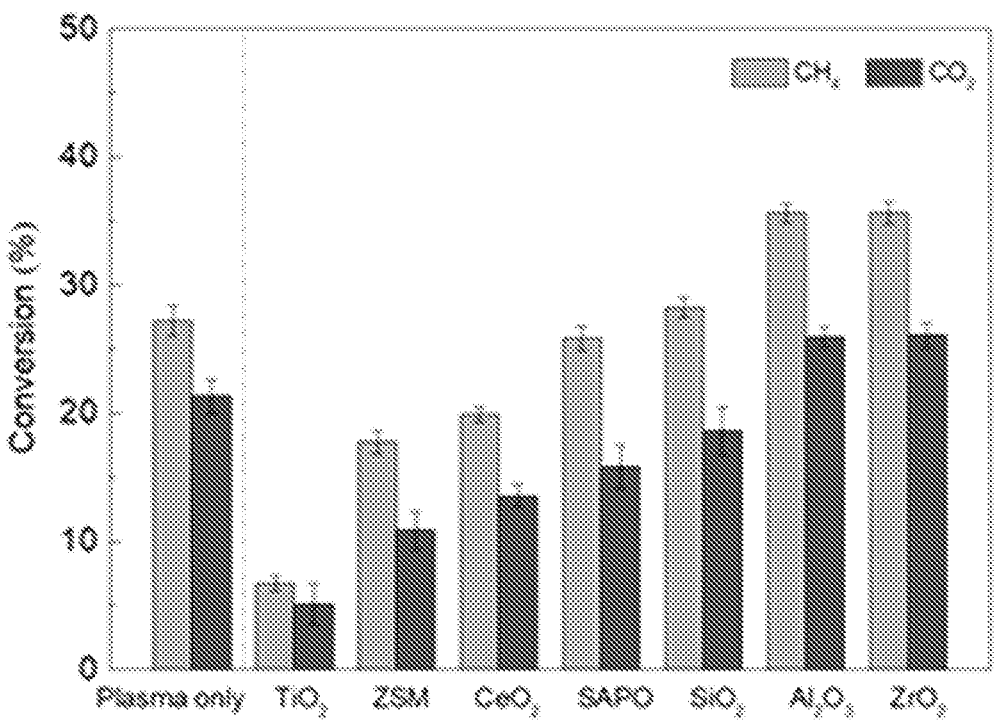
FIGS. 5A to 5D show the effect of catalyst on the synthesis of liquid products.
Figure 5B:
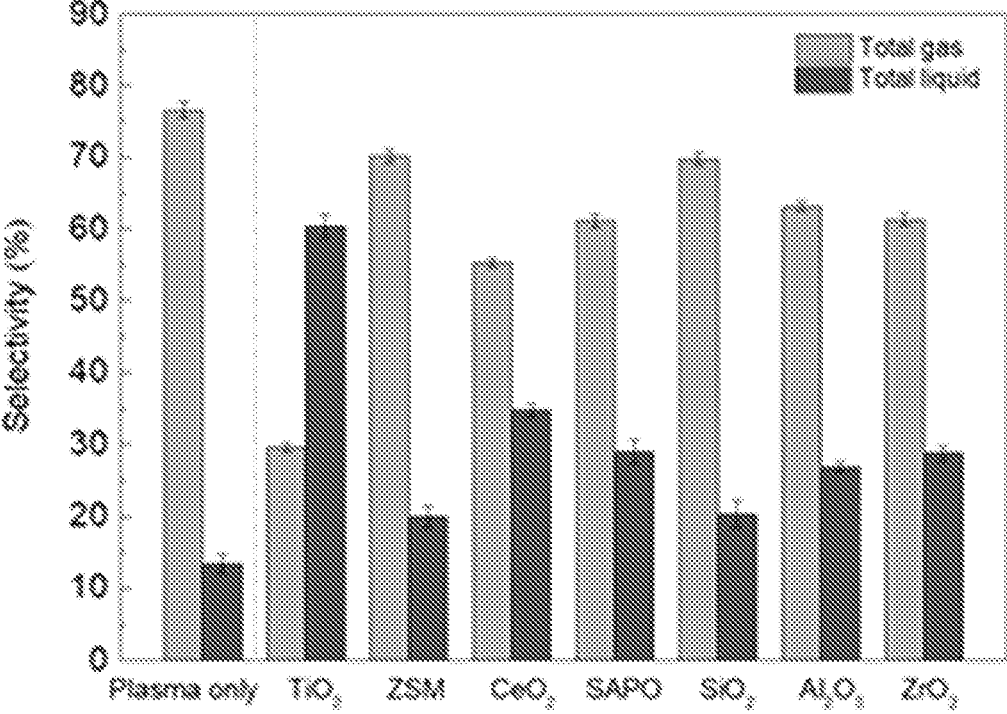
Figure 5C:
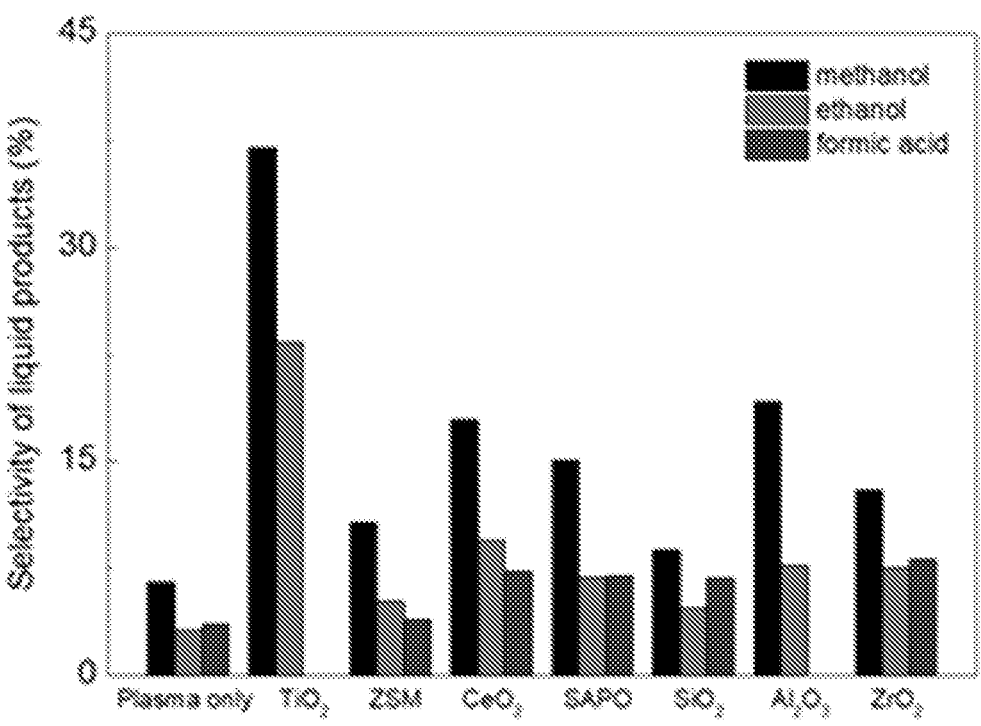
Figure 5D:
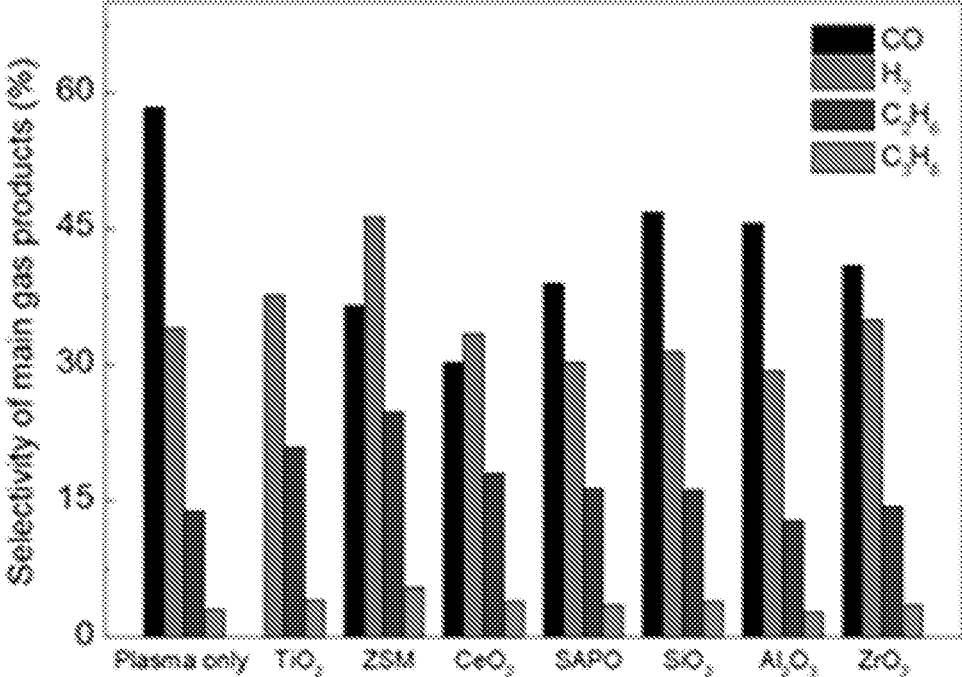
Figure 6A:
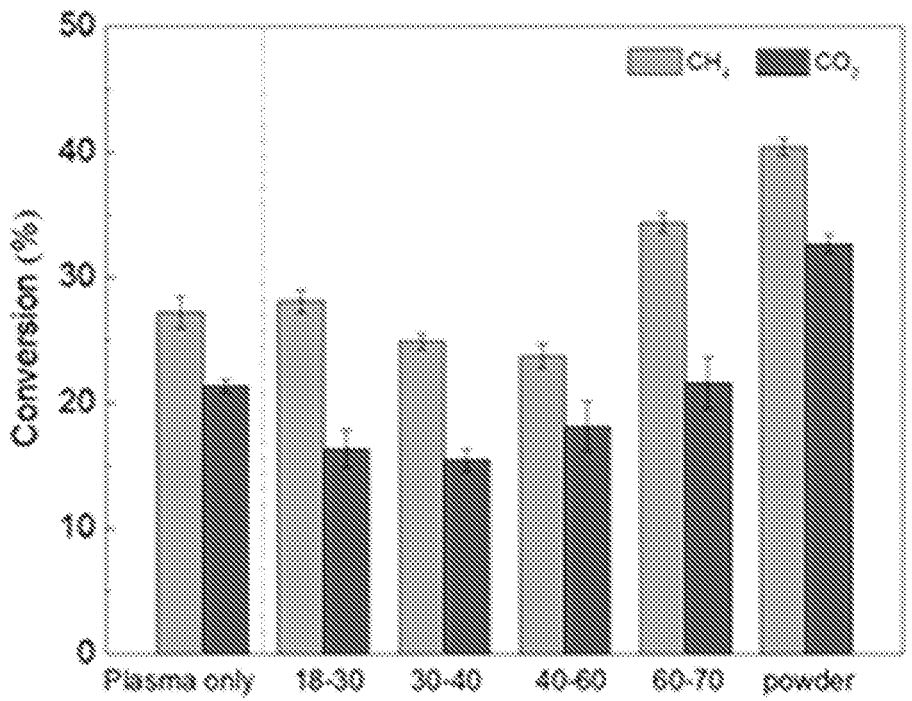
FIGS. 6A to 6D show the effect of different SiO2 packed sizes (mesh) on the reaction.
Figure 6B:
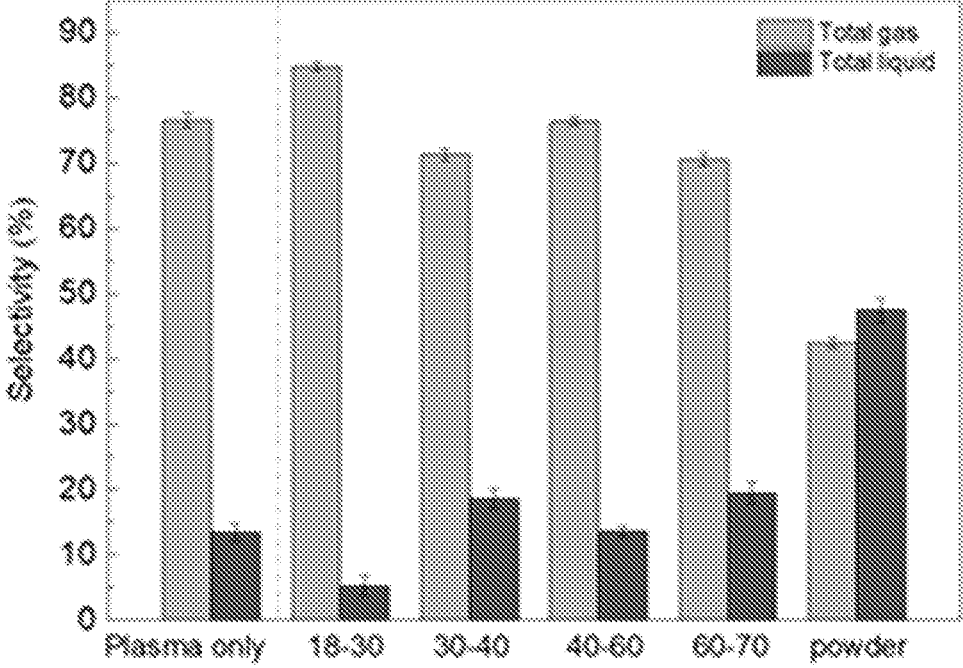
Figure 6C:
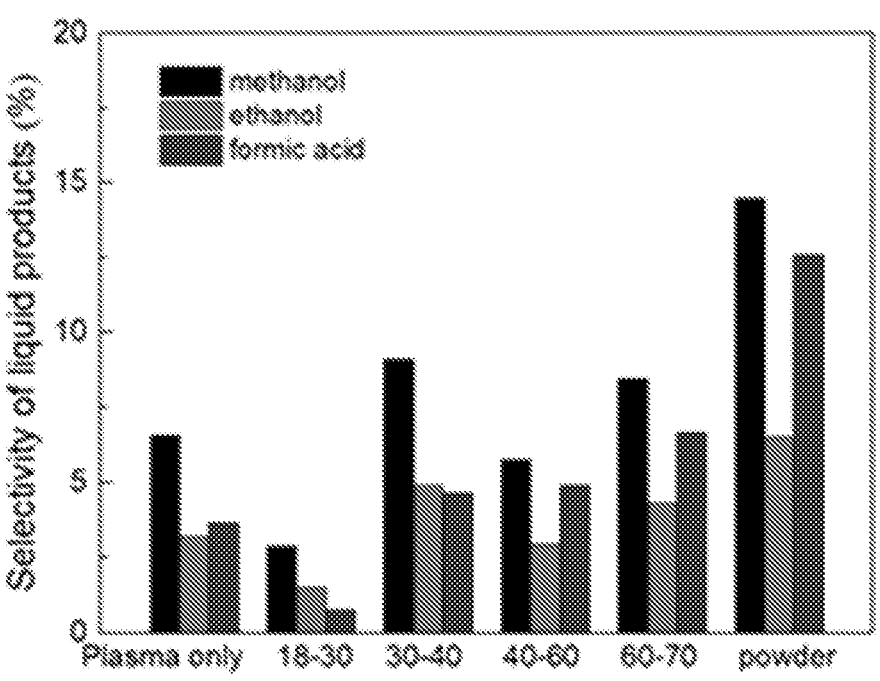
Figure 6D:
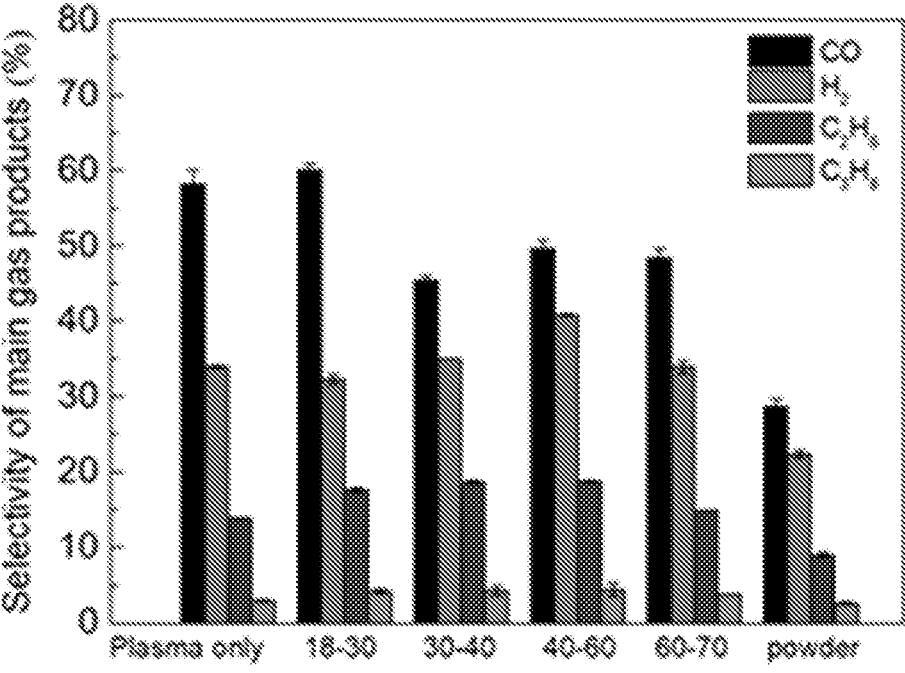

FIG. 3D shows the selectivity of methanol is not significantly affected by the change of the residence time.

FIG. 4 shows $CH_4/CO_2$ molar ratio is an important parameter affecting the conversion. The highest selectivity of liquid products is obtained at a $CH_4/CO_2$ ratio of 1:1. The highest selectivity of methanol is 38%. Increasing $CH_4/CO_2$ ratio produces more hydrocarbons such as C2-C4 due to the presence of more methane in the feed.

Example 2

The conversion of $CH_4$ and $CO_2$, and their product selectivities could be significantly influenced by the catalysts. Methanol, ethanol and formic acid are found as major liquid products. The method using $TiO_2$ as a catalyst achieves the highest liquid selectivity at 60.4%, while it also shows the lowest conversion (FIGS. 5A to 5D).

The conversions of $CO_2$ and $CH_4$ are affected by the change of the packed sizes of the catalysts.

Different sizes could considerably change the plasma properties in the discharge area, and thus influence the product selectivities.

FIGS. 6A to 6D show that the powder $SiO_2$ has the best catalytic performance for liquid product synthesis.

Example 3

Compared to the reaction using plasma only (without a catalyst), the conversion of $CH_4$ and $CO_2$ increases when using different metal oxides (including Ni, Fe, Cu, and Zn) loaded on $Al_2O_3$. And, $FeO_x/Al_2O_3$ catalyst could increase the conversion of $CH_4$ and $CO_2$ by around 5% and 10%, respectively. But there were slight decreases of both $CH_4$ and $CO_2$ when packing with $CeO_x/Al_2O_3$.

Figure 7A:
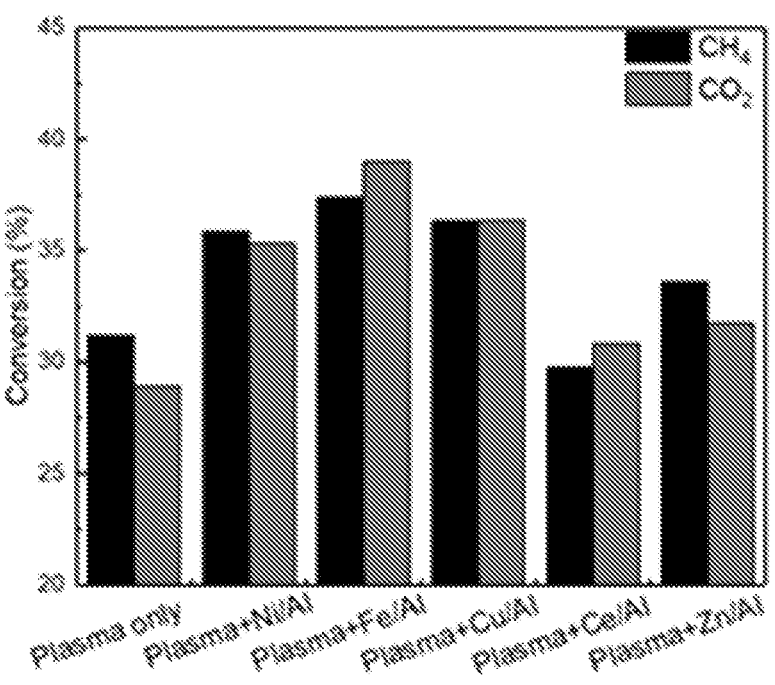
FIG. 7A shows conversion of $CO_2$ and $CH_4$.
Figure 7B:
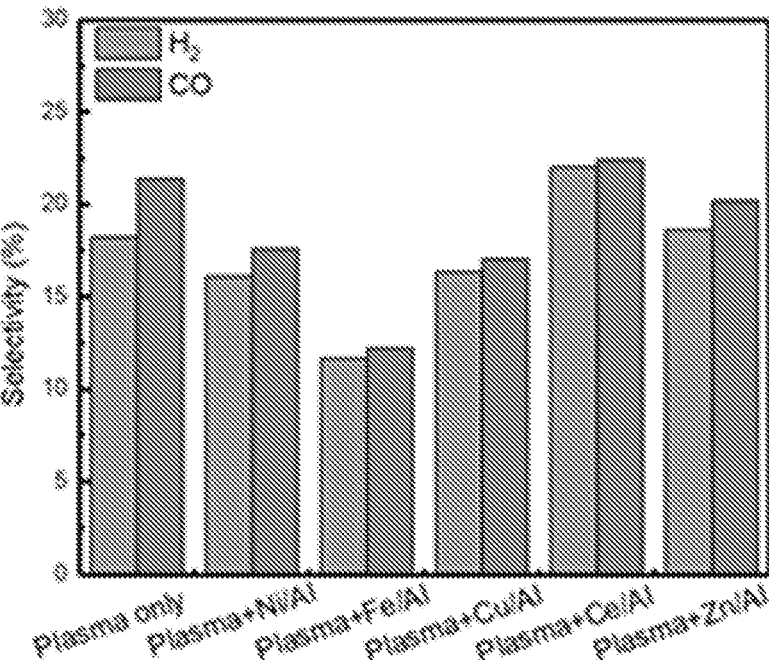
FIG. 7B shows selectivity of CO and $H_2$.
Figure 7C:
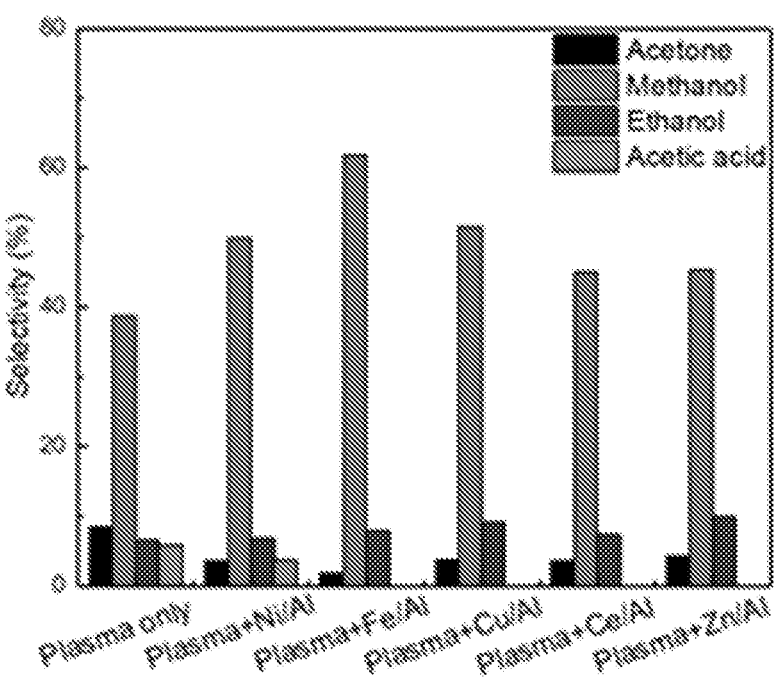
FIG. 7C shows selectivity of C2-C4 hydrocarbons.
Figure 7D:
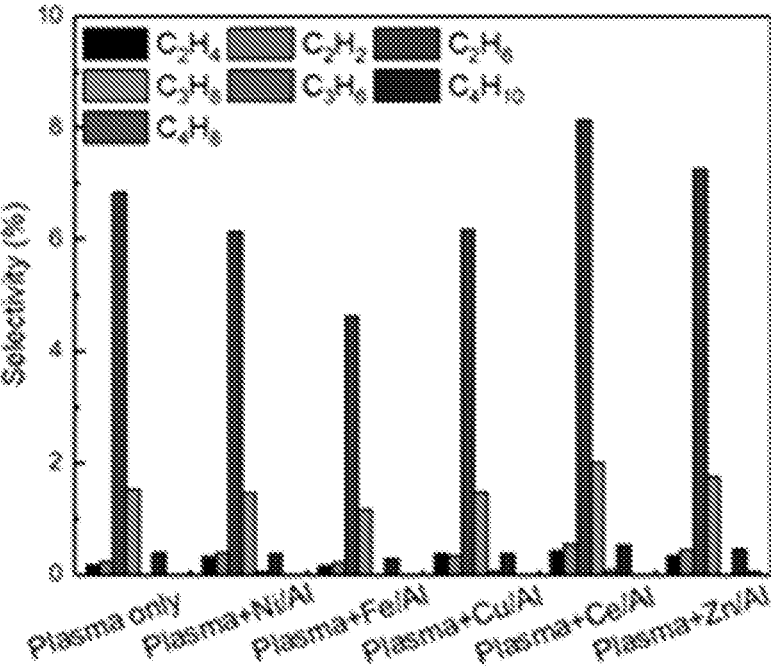
FIG. 7D shows selectivity of liquid products (M/Al refers to the metal oxides loading on $Al_2O_3$)

FIGS. 7B and 7C show the selectivity of gaseous products for the DRM reaction. CO, $H_2$ were confirmed as the main gaseous products, which could both reach a peak at around 22% when using Ce/Al catalyst. On the contrary, Fe/Al shows the lowest selectivity of gaseous products, but the highest liquid selectivity.

Methanol, ethanol, acetic acid and acetone are found as major liquid products. The highest methanol selectivity reaches 62% at a SEI of 26.3 kJ/L.

BET Results

| Samples | Metal loading (wt. %) | Surface area ($m^2/g$) | Total pore volume ($cm^3/g$) |
|---|---|---|---|
| $Al_2O_3$ | — | 221 | 0.43 |
| $NiO_x/Al_2O_3$ | 5 | 191 | 0.37 |
| $FeO_x/Al_2O_3$ | 5 | 188 | 0.36 |
| $CeO_x/Al_2O_3$ | 5 | 175 | 0.33 |
| $CuO_x/Al_2O_3$ | 5 | 182 | 0.37 |
| $ZnO_x/Al_2O_3$ | 5 | 192 | 0.37 |

XRD Analysis

Figure 8:
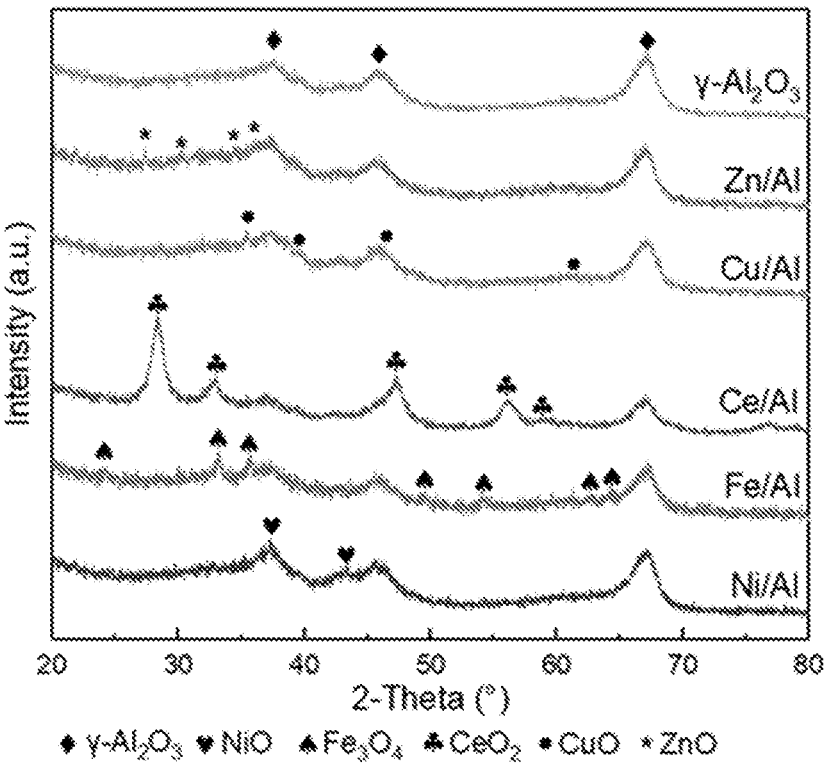
FIG. 8 shows an XRD analysis of various catalysts.

FIG. 8 shows the XRD patterns of metallic oxide catalysts, and it confirms that all of the loaded metal sites over the surface are metal oxides.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims and drawings), and/or all of the steps of any method or process so disclosed, may be combined in any combination, except combinations where at most some of such features and/or steps are mutually exclusive.

Each feature disclosed in this specification (including any accompanying claims, and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims and drawings), or to any novel one, or any novel combination, of the steps of any method or process so disclosed.

The invention claimed is:

1. An apparatus for forming a C1 to C5 oxygenate from carbon dioxide and a C1 to C4 hydrocarbon, the apparatus comprising:

a dielectric barrier discharge, DBD, device arranged to generate a plasma; and a passageway including an inlet for the carbon dioxide and the C1 to C4 hydrocarbon and an outlet for the oxygenates, wherein the passageway extends, at least in part, through the DBD device wherein, in use, the carbon dioxide and the C1 to C4 hydrocarbon are reacted in the generated plasma, thereby forming the C1 to C5 oxygenate from at least some of the carbon dioxide and the C1 to C4 hydrocarbon and wherein the DBD device comprises a conducting liquid electrode:

wherein the DBD device comprises a transition metal oxide catalyst; and wherein the transition metal oxide catalyst is iron oxide.

2. The apparatus according to claim 1, wherein the C1 to C4 hydrocarbon is selected from methane, ethane, propane and mixtures thereof.

3. The apparatus according to claim 1, wherein the liquid electrode is a water electrode or a sodium chloride electrode.

4. The apparatus according to claim 1, wherein the transition metal catalyst is held on a support selected from the group consisting of $SiO_2$, $TiO_2$, $Al_2O_3$, $CeO_2$, $ZrO_2$, ZnO, $Cr_2O_3$, carbon nanotubes, $Ga_2O_3$, $In_2O_3$ and zeolite.

5. The apparatus according to claim 1, wherein the apparatus comprises a catalyst selected from the group consisting of $TiO_2$, $CeO_2$, $SiO_2$, $Al_2O_3$, $ZrO_3$, ZSM-5 and SAPO.

6. A method of forming a C1 to C5 oxygenate from carbon dioxide and a C1 to C4 hydrocarbon, the method comprising:

generating a plasma using a dielectric barrier discharge, DBD, device; and reacting the carbon dioxide and the C1 to C4 hydrocarbon in the generated plasma, thereby forming the C1 to C5 oxygenate from at least some of the carbon dioxide and the C1 to C4 hydrocarbon; wherein the DBD device comprises a liquid electrode;

wherein the DBD device comprises a transition metal oxide catalyst; and wherein the transition metal oxide catalyst is iron oxide.

7. The method according to claim 6, wherein reacting the carbon dioxide and the C1 to C4 hydrocarbon comprises reacting the carbon dioxide and the C1 to C4 hydrocarbon at approximately ambient temperature.

8. The method according to claim 6, wherein generating the plasma using the DBD device comprises generating a stable plasma in a time in a range of from 1 to 60 minutes.

9. The method according to claim 6, wherein the conversion of carbon dioxide and/or conversion of C1 to C4 hydrocarbon is in a range from 10 to 50%.

10. The method according to claim 6, wherein the selectivity of methanol is in a range from 20 to 70%.

11. The method according to claim 6, wherein the molar ratio of carbon dioxide to C1 to C4 hydrocarbon is in a range from 1:3 to 3:1.

12. The method according to claim 6, wherein the method comprises supplying a specific energy input in a range of 15 to 60 kJ/L.

13. The apparatus of claim 1, wherein the C1 to C4 hydrocarbon is methane.

14. The apparatus of claim 1, wherein the liquid electrode is a water electrode.

* * * * *